US011241589B2

United States Patent
Li et al.

(10) Patent No.: US 11,241,589 B2
(45) Date of Patent: Feb. 8, 2022

(54) TARGET TRACKING AND IRRADIATION METHOD AND DEVICE USING RADIOTHERAPY APPARATUS AND RADIOTHERAPY APPARATUS

(71) Applicant: Our New Medical Technologies, Guangdong (CN)

(72) Inventors: Jiuliang Li, Shenzhen (CN); Hao Yan, Shenzhen (CN); Jinsheng Li, Shenzhen (CN)

(73) Assignee: OUR NEW MEDICAL TECHNOLOGIES, Shenzhen (CN)

( * ) Notice: Subject to any disclaimer, the term of this patent is extended or adjusted under 35 U.S.C. 154(b) by 0 days.

(21) Appl. No.: 16/624,881

(22) PCT Filed: Jun. 19, 2017

(86) PCT No.: PCT/CN2017/089013
§ 371 (c)(1),
(2) Date: Dec. 19, 2019

(87) PCT Pub. No.: WO2018/232568
PCT Pub. Date: Dec. 27, 2018

(65) Prior Publication Data
US 2020/0129783 A1    Apr. 30, 2020

(51) Int. Cl.
*A61N 5/10*    (2006.01)

(52) U.S. Cl.
CPC ......... *A61N 5/1037* (2013.01); *A61N 5/1067* (2013.01); *A61N 2005/1019* (2013.01); *A61N 2005/1074* (2013.01)

(58) Field of Classification Search
CPC ............... A61N 5/1037; A61N 5/1067; A61N 2005/1019; A61N 2005/1074
See application file for complete search history.

(56) References Cited

U.S. PATENT DOCUMENTS 4,503,331 A * 3/1985 Kovacs, Jr. ........... G01T 1/1648
250/363.04
5,818,902 A * 10/1998 Yu ........................ A61N 5/1047
378/65

(Continued)

FOREIGN PATENT DOCUMENTS

CN    101273896 A    10/2008
CN    101528130 A     9/2009

(Continued)

OTHER PUBLICATIONS

International search report and Written Opinion in PCT application No. PCT/CN2017/089013 dated Feb. 24, 2018.

(Continued)

*Primary Examiner* — David P Porta
*Assistant Examiner* — Djura Malevic
(74) *Attorney, Agent, or Firm* — Knobbe Martens Olson & Bear LLP

(57) ABSTRACT

A method for tracking and irradiating a target using a radiotherapy apparatus, a device and a radiotherapy apparatus are provided. The radiotherapy apparatus includes a first ray source, a second ray source, and at least one detector. The method includes: moving the first ray source to a first location to emit a ray beam; receiving the ray beam emitted from the first ray source at the first location and generating first image data of a target according to the received ray beam, by the detector; and adjusting the second ray source according to the first image data to make the second ray source move to the first location and an emitted ray beam pass through the target, wherein a time taken for the second ray source to move to the first location is a positive integer multiple of a preset respiratory period of a patient.

16 Claims, 10 Drawing Sheets

(56) References Cited

U.S. PATENT DOCUMENTS

| | | | | |
|---|---|---|---|---|
| 6,385,288 B1* | 5/2002 | Kanematsu | A61N 5/1042 | 378/65 |
| 6,934,363 B2* | 8/2005 | Seufert | G21K 1/04 | 378/147 |
| 6,976,784 B2* | 12/2005 | Kojima | G01T 1/1648 | 378/197 |
| 7,154,096 B2* | 12/2006 | Amano | A61B 6/032 | 250/363.03 |
| 7,297,958 B2* | 11/2007 | Kojima | A61B 6/4241 | 250/363.03 |
| 7,627,084 B2* | 12/2009 | Jabri | A61B 6/4035 | 378/154 |
| 7,924,971 B2* | 4/2011 | Knox | A61B 6/5217 | 378/8 |
| 7,997,799 B2* | 8/2011 | Jabri | A61B 6/482 | 378/205 |
| 8,017,915 B2* | 9/2011 | Mazin | A61B 6/037 | 250/363.04 |
| 8,229,068 B2* | 7/2012 | Lu | A61N 5/1049 | 378/65 |
| 8,379,792 B2* | 2/2013 | Saito | A61B 6/032 | 378/8 |
| 8,461,538 B2* | 6/2013 | Mazin | G01T 1/2985 | 250/363.04 |
| 8,748,825 B2* | 6/2014 | Mazin | A61N 5/1067 | 250/363.04 |
| 9,205,281 B2* | 12/2015 | Mazin | A61B 6/469 | |
| 9,283,403 B2* | 3/2016 | Mazin | A61B 6/037 | |
| 9,504,850 B2* | 11/2016 | Zhang | A61B 5/0036 | |
| 9,636,525 B1 | 5/2017 | Sahadevan | | |
| 9,649,509 B2* | 5/2017 | Mazin | A61B 6/469 | |
| 9,694,208 B2* | 7/2017 | Mazin | A61B 5/055 | |
| 9,731,148 B2* | 8/2017 | Olivera | A61B 6/08 | |
| 9,764,161 B2* | 9/2017 | Mazin | A61B 5/055 | |
| 9,820,700 B2* | 11/2017 | Mazin | G01T 1/2985 | |
| 9,848,835 B2* | 12/2017 | Berkus | A61B 6/541 | |
| 10,143,857 B2* | 12/2018 | Mazin | A61N 5/1048 | |
| 10,159,852 B2* | 12/2018 | Mazin | A61N 5/1039 | |
| 10,327,716 B2* | 6/2019 | Mazin | A61B 6/541 | |
| 10,433,760 B2* | 10/2019 | Brown | A61M 16/021 | |
| 10,434,332 B2* | 10/2019 | Vilsmeier | A61B 6/50 | |
| 10,695,583 B2* | 6/2020 | Mazin | A61B 6/037 | |
| 10,695,586 B2* | 6/2020 | Harper | A61N 5/1081 | |
| 10,702,715 B2* | 7/2020 | Pearce | A61N 5/107 | |
| 2002/0191734 A1* | 12/2002 | Kojima | A61B 6/037 | 378/4 |
| 2004/0218719 A1* | 11/2004 | Brown | G06T 7/0016 | 378/95 |
| 2007/0003010 A1* | 1/2007 | Guertin | A61N 5/1069 | 378/63 |
| 2007/0014391 A1* | 1/2007 | Mostafavi | A61B 6/5247 | 378/63 |
| 2007/0025496 A1* | 2/2007 | Brown | G06T 5/003 | 378/8 |
| 2007/0211857 A1* | 9/2007 | Urano | A61N 5/1049 | 378/65 |
| 2007/0221869 A1* | 9/2007 | Song | A61N 5/1081 | 250/492.1 |
| 2008/0031404 A1* | 2/2008 | Khamene | A61B 6/032 | 378/6 |
| 2008/0130825 A1* | 6/2008 | Fu | G06T 7/248 | 378/8 |
| 2008/0152085 A1* | 6/2008 | Saracen | A61N 5/1038 | 378/65 |
| 2008/0205588 A1* | 8/2008 | Kim | A61B 6/4447 | 378/20 |
| 2008/0240357 A1* | 10/2008 | Jabri | A61B 6/482 | 378/101 |
| 2008/0253516 A1* | 10/2008 | Hui | A61B 6/4007 | 378/62 |
| 2008/0273659 A1* | 11/2008 | Guertin | A61N 5/1049 | 378/65 |
| 2008/0298536 A1* | 12/2008 | Ein-Gal | A61B 6/0421 | 378/4 |
| 2009/0086909 A1* | 4/2009 | Hui | A61N 5/1084 | 378/65 |
| 2009/0116616 A1* | 5/2009 | Lu | A61N 5/1049 | 378/65 |
| 2009/0256078 A1* | 10/2009 | Mazin | A61B 6/54 | 250/362 |
| 2010/0046705 A1* | 2/2010 | Jabri | A61B 6/482 | 378/62 |
| 2010/0067660 A1* | 3/2010 | Maurer, Jr. | A61B 6/541 | 378/95 |
| 2010/0095959 A1* | 4/2010 | Farrell | A61M 16/024 | 128/202.13 |
| 2010/0104070 A1* | 4/2010 | Knox | A61B 6/5217 | 378/95 |
| 2011/0073763 A1* | 3/2011 | Subbarao | A61B 6/037 | 250/362 |
| 2011/0272600 A1* | 11/2011 | Bert | A61N 5/103 | 250/492.1 |
| 2011/0309255 A1* | 12/2011 | Bert | A61N 5/1048 | 250/363.03 |
| 2012/0123183 A1* | 5/2012 | Lavi | A61N 5/103 | 600/1 |
| 2012/0230464 A1* | 9/2012 | Ling | A61B 6/4085 | 378/9 |
| 2014/0228613 A1* | 8/2014 | Mazin | A61N 5/1048 | 600/1 |
| 2014/0249348 A1* | 9/2014 | Mazin | A61N 5/1067 | 600/1 |
| 2016/0361570 A1* | 12/2016 | Sayeed | A61N 5/1071 | |
| 2020/0234443 A1* | 7/2020 | Yan | G06T 7/0014 | |

FOREIGN PATENT DOCUMENTS

| | | |
|---|---|---|
| CN | 101623198 A | 1/2010 |
| CN | 102415897 A | 4/2012 |
| CN | 203220692 U | 10/2013 |
| CN | 103650095 A | 3/2014 |
| CN | 104220132 A | 12/2014 |
| CN | 104258508 A | 1/2015 |
| CN | 106029171 A | 10/2016 |
| CN | 106237545 A | 12/2016 |
| CN | 106310528 A | 1/2017 |
| CN | 106777976 A | 5/2017 |

OTHER PUBLICATIONS

First Office Action of Chinese Patent Application No. 201780091224. X—18 pages (dated Nov. 4, 2020).

The Second Office Action of Chinese Patent Application No. 201780091224.X—17 pages (dated May 18, 2021).

* cited by examiner

TARGET TRACKING AND IRRADIATION METHOD AND DEVICE USING RADIOTHERAPY APPARATUS AND RADIOTHERAPY APPARATUS

CROSS-REFERENCE TO RELATED APPLICATION

This application is a 371 of PCT international patent application No.: PCT/CN2017/089013 filed on Jun. 19, 2017.

TECHNICAL FIELD

The present disclosure relates to the field of radiotherapy instruments, and more specifically, to a therapy apparatus and a control method.

BACKGROUND

One of the key factors of radiotherapy is to keep precise positioning of a tumor during treatment. For example, because a lung tumor moves with respiration, it is extremely difficult to keep precise positioning of the tumor at all times. Real-time tumor tracking becomes a very challenging problem. In the existing methods, one way is to monitor external surrogate signals associated with respiration and use this as a basis to predict the movement of a tumor. The external surrogate signals include the up and down movement of a patient's body surface marker, the increase or decrease of the amount of gas breathed by the patient, or the change of the patient's abdominal pressure. However, the external surrogate signals cannot accurately characterize the movement of the tumor and there is a high uncertainty. Moreover, a number of researches show that there is a phase shift between the external surrogate signal and the movement of a tumor, the amplitude of the shift changes with a patient's respiration, and the shift is unpredictable and practically inevitable. The other method is to directly perform a perspective imaging of the tumor region, and inversely calculate the 3D position of the tumor in space by 2D locations of a tumor in two X-ray projections that are at an angle with each other. A tumor is usually implanted with a plurality of metal markers before imaging to compensate for insufficient contrast in a perspective projection of the tumor. A tumor has relatively low contrast in a fluoroscopic image and cannot be directly observed in most cases. The tumor is usually implanted with a plurality of metal markers before imaging to enhance the contrast. The implantation of metal markers brings additional surgical pains to a patient and is very likely to induce conditions such as "pneumothorax". In addition, the metal markers may be relatively moved with time, which brings a higher error to the position determination. Without the implantation of metal markers, limited visibility of detection imaging will result in extremely low accuracy in tumor tracking. None of the above methods can accurately realize the real-time tracking of the tumor location during treatment in clinical application. As a result, when formulating a treatment plan, doctors have no choice but to distribute a prescribed dose to an expanded irradiation region that covers a movement range of a tumor to ensure that the tumor is always inside the irradiation range during treatment. However, this method results in inadequate irradiation of the tumor itself, and at the same time leads to additional irradiation of normal organs around the tumor and damage is caused.

Therefore, how to make a tumor to be always irradiated by a ray beam, avoid normal tissue from being irradiated and reduce damage to the normal tissue becomes a problem that urgently needs to be resolved in this field.

SUMMARY

An objective of the present disclosure is to provide a target tracking and irradiation method and device using a radiotherapy apparatus and a radiotherapy apparatus, so as to make a tumor to be always irradiated by a ray beam, avoid normal tissue from being irradiated and reduce the damage to the normal tissue.

The objective of the present disclosure is implemented by using the following technical solution:

There is a target tracking and irradiation method using a radiotherapy apparatus, the radiotherapy apparatus including a first ray source, a second ray source, and at least one detector; the method including:

moving the first ray source to a first location to emit a ray beam; receiving the ray beam emitted from the first ray source at the first location and generating first image data of a target according to the received ray beam, by the detector; and adjusting the second ray source according to the first image data to make the second ray source move to the first location and an emitted ray beam pass through the target, wherein a time taken for the second ray source to move to the first location is a positive integer multiple of a preset respiratory period of a patient.

The present disclosure discloses a target tracking and irradiation device using a radiotherapy apparatus, the radiotherapy apparatus including a first ray source, a second ray source, and at least one detector; the device including: a first controller, configured to control the movement of the first ray source, wherein the first ray source moves to a first location to emit a ray beam; a second controller, configured to control the detector to receive the ray beam emitted by the first ray source at the first location, and generate first image data of a target according to the received ray beam; and a third controller, configured to receive the first image data of the detector, and adjust the second ray source according to the first image data to make the second ray source move to the first location and an emitted ray beam pass through the target, wherein the third controller is further configured to control a time taken for the second ray source to move to the first location to be a positive integer multiple of a preset respiratory period of a patient.

The present disclosure discloses a radiotherapy apparatus, including the device according to any one of the foregoing.

According to the target tracking and irradiation method using a radiotherapy apparatus in the present disclosure, the radiotherapy apparatus includes a first ray source, a second ray source, and at least one detector. The method includes: moving the first ray source to a first location to emit a ray beam; receiving the ray beam emitted from the first ray source at the first location and generating first image data of a target according to the received ray beam, by the detector; and adjusting the second ray source according to the first image data to make the second ray source move to the first location and an emitted ray beam pass through the target, wherein a time taken for the second ray source to move to the first location is a positive integer multiple of a preset respiratory period of a patient. In this manner, the first ray source emits a ray beam at the first location, the detector receives the ray beam to form first image data of a target, the second ray source is then adjusted according to the first image data, and the second ray source is controlled to move to the first location to emit a ray beam. Because the time taken for the second ray source to move to the first location is a positive integer multiple of a preset respiratory period of a patient, a node during an irradiation of the first ray source emits radiation and a node during an irradiation of the second ray source emits radiation are the same nodes within different respiratory periods. Therefore, when the second ray source is in the first position to irradiate the target, a state of the target is very similar to a state of the target when receiving the radiation from the first ray source. Therefore, controlling the second ray source to irradiate the target with reference to the first image data greatly reduces the errors caused by the patient's respiration are greatly reduced, and more accurately irradiates target the location, so that a ray beam can always irradiate the location of a tumor and normal tissue is avoided from being irradiating and thus damage to the normal tissue is reduced.

DETAILED DESCRIPTION

Although a flow chart may describe the operations as a sequential process, many of the operations may be performed in parallel, concurrently or simultaneously. The order of the operations may be rearranged. A process may be terminated when its operations are completed, but may have additional steps not included in the figures. A process may correspond to a method, function, procedure, subroutine, subprogram or the like.

Computer equipment includes user equipment and network equipment. The user equipment or a client includes, but is not limited to, a computer, a smart phone or a personal digital assistant (PDA). The network equipment includes, but is not limited to, a single network server, a server group formed by a plurality of network servers or a cloud that is based on cloud computing and is formed by a large number of computers or network servers. The computer equipment may be separately run to implement the present disclosure or may be connected to a network and interact with other computer equipment in the network to implement the present disclosure. The network that the computer equipment includes, but is not limited to, the Internet, a wide area network, a metropolitan area network, a local area network or a virtual private network (VPN).

The terms "first", "second", and the like may be used herein to describe the units. However, these units should not be limited by these terms. These terms are only used for distinguishing one unit from another. The term "and/or" used herein includes any and all combinations of one or more associated listed items. When one unit is referred to as being "connected" or "coupled" to another unit, the unit may be directly connected or coupled to the another unit or an intervening unit may be present.

The terms used herein are only intended to describe specific embodiments rather than to limit the exemplary embodiments. The singular forms "a" and "an" are also intended to include the plural meaning unless otherwise indicated clearly in the context. It should further be understood that the terms "include" and/or "comprise" used herein specifies the existence of the discussed features, integers, steps, operations, units and/or components, but does not exclude the existence or addition of one or more other features, integers, steps, operations, units, components and/or combinations thereof.

The present disclosure is further described below with reference to the accompanying drawings and preferred embodiments.

Figure 1:
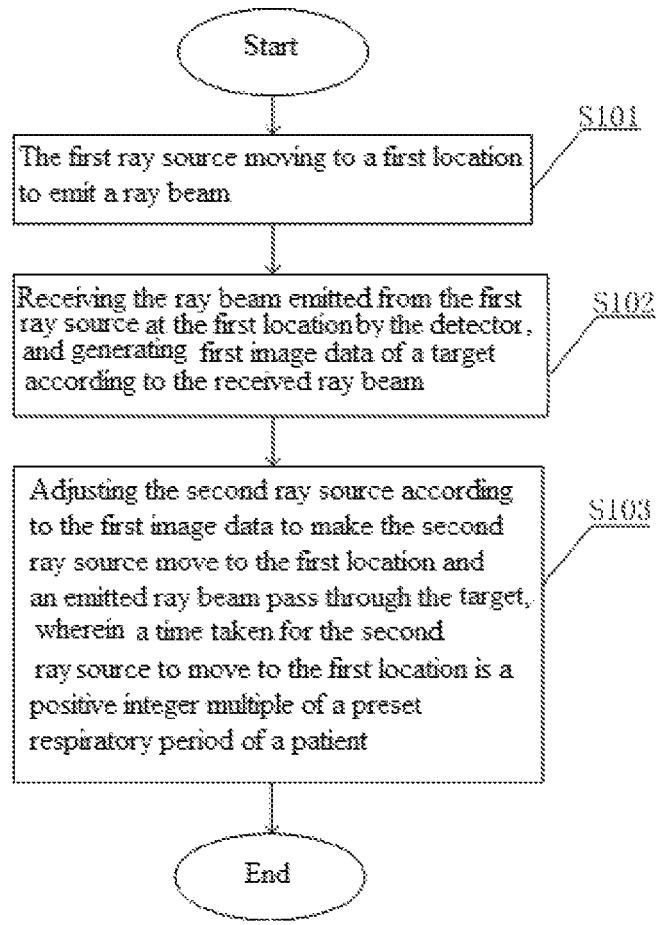
FIG. 1 is a flowchart of a target tracking and irradiation method using a radiotherapy apparatus according to an embodiment of the present disclosure.

As shown in FIG. 1, the present embodiment discloses a target tracking and irradiation method using a radiotherapy apparatus. The radiotherapy apparatus includes a first ray source, a second ray source, and at least one detector. The method includes the following steps S101-S103.

In S101, the first ray source moves to a first location to emit a ray beam.

In S102, the detector receives the ray beam emitted from the first ray source at the first location, and generates first image data of a target according to the received ray beam.

In S103, the second ray source is adjusted according to the first image data to make the second ray source move to the first location and an emitted ray beam pass through the target.

A time taken for the second ray source to move to the first location is a positive integer multiple of a preset respiratory period of a patient.

In this manner, the first ray source emits a ray beam at the first location, the detector receives the ray beam to form first image data of a target, the second ray source is then adjusted according to the first image data, and the second ray source is controlled to move to the first location to emit a ray beam. Because the time taken for the second ray source to move to the first location is a positive integer multiple of a preset respiratory period of a patient, a node during an irradiation of the first ray source emits radiation and a node during an irradiation of the second ray source emits radiation are the same nodes within different respiratory periods. Therefore, when the second ray source is in the first position to irradiate the target, a state of the target is very similar to a state of the target when receiving the radiation from the first ray source. Therefore, controlling the second ray source to irradiate the target with reference to the first image data greatly reduces the errors caused by the patient's respiration and more accurately irradiates the target location, so that a ray beam can always irradiate the location of a tumor and normal tissue is avoided from being irradiating and thus damage to the normal tissue is reduced.

In the present embodiment, fixing manners and movement manners of the first ray source and the second ray source are not specifically limited. The first ray source may be mounted on a cantilever or mounted on a C-shaped beam or mounted on an annular support or mounted on a drum, and the second ray source may be mounted on a cantilever or mounted on a C-shaped beam or mounted on an annular support or mounted on a drum or mounted in another manner, provided that the first ray source can be controlled to move to the first location and the second ray source can be controlled to move to the first location. It should be noted that the present embodiment is not limited to that the first ray source and the second ray source are mounted on a drum. Instead, the first ray source and the second ray source may be separately mounted on other structures, for example, a cantilever, a C-shaped beam, an annular support or a drum. Alternatively, the first ray source and the second ray source may both be mounted on a structure, for example, a cantilever, a C-shaped beam, an annular support or a drum. The first ray source and the second ray source may be flexibly mounted as required.

In the present embodiment, a manner in which the detector receives a ray beam and the number of detectors are not specifically limited. The detector may be disposed to be movable. For example, one detector moves relative to the first ray source, and another detector moves relative to the second ray source. Alternatively, the detector may be disposed at a fixed position. For example, the detector always remains at a location opposite to the first location to receive ray beams from the first ray source and the second ray source. Only one detector is disposed. When one detector is disposed, the detector may be disposed at a fixed position or may be movable. Certainly, two detectors may be disposed. One detector receives a ray beam emitted from the first ray source at the first location, and the other detector receives a ray beam emitted from the second ray source at the first location. The number of detectors is not specifically limited in the present disclosure. It may be two or three or more than three. In the present embodiment, the first ray source may be a radioactive source that emits a kilovoltage (KV) ray or certainly may be other type of radioactive source, for example, a megavoltage (MV) radioactive source or other type of radioactive source. The second ray source may be a radioactive source that emits a KV ray or certainly may be other type of radioactive source, for example, an MV radioactive source or other type of radioactive source.

In an example of the present embodiment, the first ray source may be a KV imaging source and the second ray source may be a KV imaging source. The target is irradiated at the first location. The detector receives a ray beam from the first ray source to obtain first image data. Subsequently, the second ray source reaches the first location according to the first image data in a time that is a positive integer multiple of the respiratory period of the patient and emits a ray beam. The detector receives the ray beam from the second ray source and obtains second image data. In this way, when the second ray source reaches the first location and emits a ray beam to the target, adjustments may be made according to the first image data. The adjustments include adjusting an irradiation angle, a dosage, a dose distribution, and the like. In addition, the time of emitting the ray beams is the same nodes within different respiratory periods of the patient, which reduces ray beam errors when the second ray source irradiates the target, improves the accuracy of the irradiation of a diseased position, reduces the irradiation to normal tissue and protects a normal part and physical health of the patient.

In an example of the present embodiment after the second image data is generated, a step of confirming the first image data and the second image data may further be performed in the method of the present embodiment. In this way, it can be verified whether the patient's tumor location, respiratory period, and the like change. For example, if there is only a slight change, treatment may continue. If there is a considerable change, it may be necessary to suspend treatment or change a treatment solution to continue to treat the patient more precisely.

In an example of the present embodiment, the first ray source may be a KV imaging source, and the second ray source may be an MV treatment source. The target is irradiated at the first location, and the detector receives a ray beam from the first ray source to obtain first image data. Subsequently, the second ray source reaches the first location according to the first image data in a time that is a positive integer multiple of the respiratory period of the patient and emits a treatment ray beam used to treat a diseased part of the patient. In this way, when the second ray source reaches the first location and emits a ray beam to the target, adjustments may be made according to the first image data. The adjustments include adjusting an irradiation angle, a dosage, a dose distribution, and the like. In addition, the time of emitting the ray beams is the same nodes within different respiratory periods of the patient, which reduces ray beam errors when the second ray source irradiates and treats the target, improves the accuracy of the irradiation of a diseased position, reduces the irradiation to normal tissue and protects a normal part and physical health of the patient.

Figure 2:
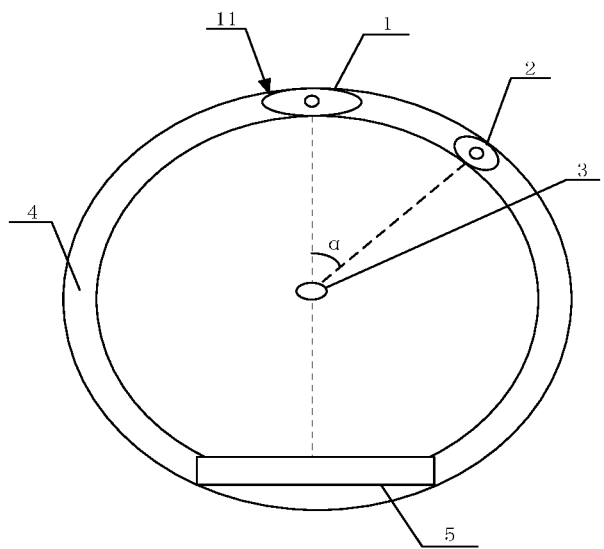
FIG. 2 is a schematic diagram showing that a first ray source is located at a first location according to an embodiment of the present disclosure.

As shown in FIG. 2, in the present embodiment, a first ray source 1 and a second ray source 2 are mounted on a drum 4 as an example for description. The first ray source and the second ray source may be driven by the drum to move. Alternatively, the first ray source and the second ray source may move relative to the drum. In the present disclosure, the first ray source and the second ray source are driven by the drum to move as an example for description. The first ray source 1 and the second ray source 2 may rotate around a target 3 in a circumferential direction. A detector 5 may receive a ray beam emitted from the first ray source 1. An angle between the first ray source 1 and the second ray source 2 is $\alpha$, wherein $0° \leq \alpha \leq 180°$. In the present embodiment, the angle $\alpha$ between the first ray source 1 and the second ray source 2 is usually a constant value, such that the ray sources are conveniently controlled to facilitate imaging and treatment. Certainly, the angle $\alpha$ may be not constant, and it may be variable.

Figure 3:
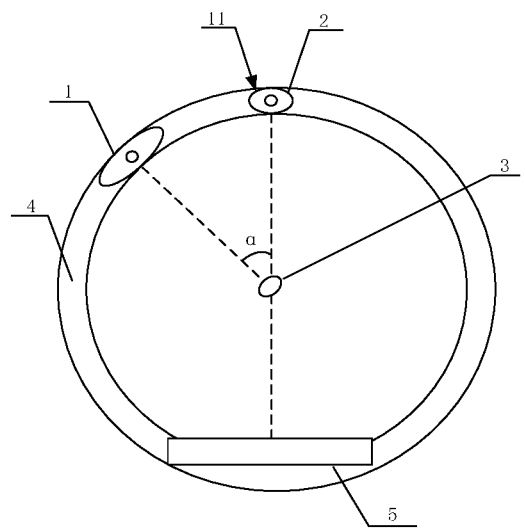
FIG. 3 is a schematic diagram showing that a second ray source is located at a first location according to an embodiment of the present disclosure.

As shown in FIG. 2, the first ray source 1 emits a ray beam at a first location 11 to irradiate the target 3. The detector 5 receives the ray beam emitted from the first ray source 1 at the first location 11 and passing through the target 3 and generates first image data of the target according to the ray beam. As shown in FIG. 3, the second ray source 2 is controlled according to the first image data to move to the first location 11. A time taken for the second ray source 2 to move to the first location 11 is a positive integer multiple of a preset respiratory period of a patient. The second ray source 2 emits a ray beam at the first location 11 to irradiate the target. An irradiation range, a dosage, and the like of the second ray source 2 are adjusted based on the first image data, and the time of emitting the ray beams is the same nodes within different respiratory periods of the patient, which reduce ray beam errors when the second ray source irradiates the target, improve the accuracy of the irradiation of a diseased position and reduce the irradiation to normal tissue.

Figure 4:
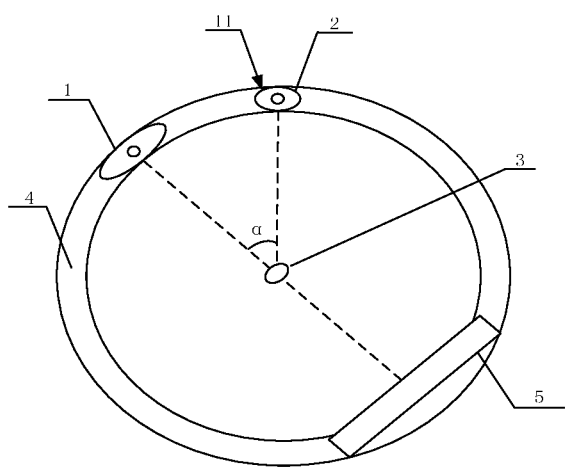
FIG. 4 is another schematic diagram showing that a second ray source is located at a first location according to an embodiment of the present disclosure.

In an example of the present embodiment, as shown in FIG. 3, the second ray source 2 may emit an imaging ray beam. The detector 5 receives, at an opposite location of the first location 1, the imaging ray beam emitted from the second ray source 2, and generates second image data according to the imaging ray beam. The first image data and the second image data are acquired at the same nodes within different respiratory periods of the patient, and thus it can be accordingly determined whether the status, respiratory period, and the like of the patient change, and the value of a current respiratory period of the patient can further be determined according to the extent of the change so as to learn about the patient's status in time. Certainly, the second ray source 2 may also emit a treatment ray beam. The detector 5 may receive, at the opposite location of the first location 1, the ray beam from the second ray source 2. In an example of the present embodiment, as shown in FIG. 4, when the second ray source 2 moves to the first location 11, the detector 5 may move along with the location of the first ray source 1 and move to the location opposite to the first ray source 1. The second ray source 2 may emit an imaging ray beam, and other detector receives the imaging ray beam for imaging. The second ray source 2 may also emit a treatment ray beam. The first ray source 1 may continue to emit a ray beam to irradiate the target 3. The detector 5 may receive the ray beam from the first ray source 1 to form image data of another location. The second ray source 2 may irradiate the target 3 according to the image data at such another location to perform more accurate imaging or treatment.

Figure 5:
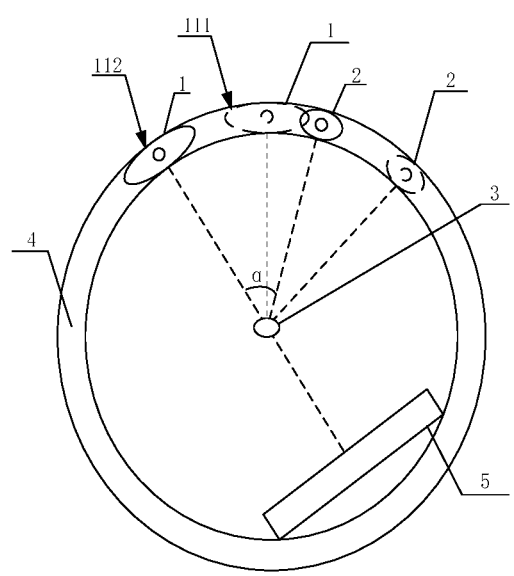
FIG. 5 is a schematic diagram of a plurality of first locations according to an embodiment of the present disclosure.

In the present embodiment, the first location is not limited to the location shown in the drawings, and may be other location on the circumference or a location on other structure. For example, it may move to a certain position driven by a cantilever or a C-shaped beam. The first location is also not limited to have only one location in the present embodiment. For example, the first location may be a plurality of different locations within one respiratory period. In this case, a plurality of first image data are acquired at the plurality of locations within the respiratory period, and the second ray source is adjusted according to first image data at the plurality of locations within the respiratory period. In a case that the second ray source is a treatment source, a real-time image-guided precise treatment can be realized. For example, as shown in FIG. 5, the first location includes a first first location 111 and a second first location 112. The first ray source 1 may move to the first first location 111 and the second first location 112. In this way, the detector 5 obtains more accurate first image data according to ray beams from the first ray source 1 at the first first location 111 and the second first location 112. As the first ray source 1 moves, the second ray source 2 may move synchronously to keep the same angle α from the first ray source 1. Certainly, the first ray source 1 and the second ray source 2 may move asynchronously.

Figure 6:
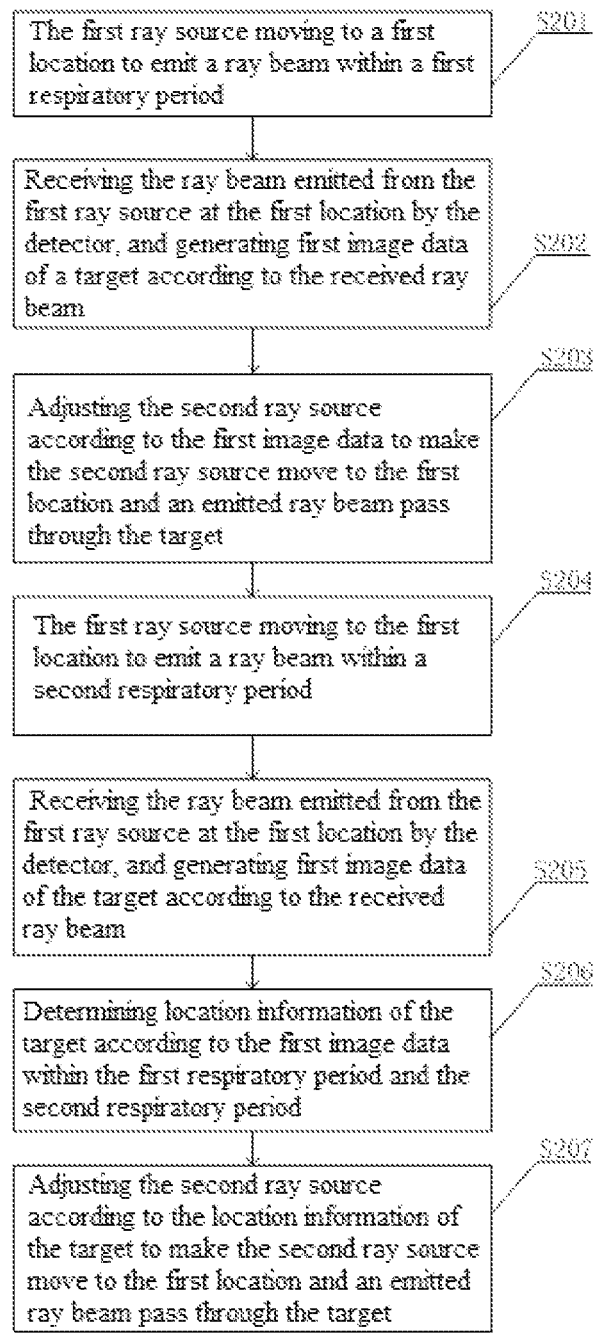
FIG. 6 is a flowchart of another target tracking and irradiation method using a radiotherapy apparatus according to an embodiment of the present disclosure.

For example, the first location may include at least two different locations. The present embodiment discloses a target tracking and irradiation method using a radiotherapy apparatus. What is shown in FIG. 1 is used as an example. As shown in FIG. 6, the method includes the following steps S201-S207.

In S201, within a first respiratory period, the first ray source moves to a first location to emit a ray beam.

In S202, the detector receives the ray beam emitted from the first ray source at the first location, and generates first image data of a target according to the received ray beam.

In S203, the second ray source is adjusted according to the first image data to make the second ray source move to the first location and an emitted ray beam pass through the target.

In S204, within a second respiratory period, the first ray source moves to the first location to emit a ray beam.

In S205, the detector receives the ray beam emitted from the first ray source at the first location, and generates first image data of the target according to the received ray beam.

In S206, location information of the target is determined according to the first image data within the first respiratory period and the second respiratory period.

In S207, the second ray source is adjusted according to the location information of the target to make the second ray source move to the first location and an emitted ray beam pass through the target.

In an embodiment provided by the present disclosure, first image data within at least two different respiratory periods is acquired, location information of the target is determined according to the first image data within the different respiratory periods, and the second ray source is adjusted according to the location information of the target. The first image data within two different respiratory periods is used to precisely acquire the location information of the target, and then to adjust the second ray source according to the location information, so as to make the second ray source to irradiate the location of the target more accurately, and to reduce damage to normal tissue. The first location within the first respiratory period and the first location within the second respiratory period may be the same locations or may be different locations. For example, the first location within the first respiratory period may be a corresponding location at an inhalation node, and the first location within the second respiratory period may be a corresponding location at an exhalation node.

The different respiratory periods may be two adjacent respiratory periods or three or more than three adjacent respiratory periods or any two or three or more than three nonadjacent respiratory periods. For example, the different respiratory periods are two adjacent respiratory periods. In this case, it may be determined whether the respiratory period of the patient changes within a short time and the detail of the change can be found out. For another example, the different respiratory periods are three or more than three adjacent respiratory periods. In this case, a change in the respiratory period and the value of the current respiratory period of the patient are more accurately obtained by comparing more image data. For another example, the different respiratory periods are any two nonadjacent respiratory periods. In this case, respiratory changes of the patient within the different periods of time are obtained by comparing the respiratory periods of the patient within different periods of time, so as to provide more rich data for treatment. For another example, the different respiratory periods are any three or more than three nonadjacent respiratory periods. In this case, more changes in the respiratory periods of the patient within different periods of time can be obtained, so as to learn more precisely about changes in the pathological status of the patient.

In the present embodiment, the respiratory period includes three parts, namely, inhalation, exhalation, and breath holding. The inhalation is an active process of inhaling air to fill the lungs with clean and fresh air. The exhalation is a passive process of breathing to exhaust stale air and empty the lungs. The breath holding is a normal pause between inhalation and exhalation. The breath holding includes two parts, namely, breath holding after inhalation and breath holding after exhalation. The respiratory period of the patient is a time taken to complete the three parts, that is, to complete the entire process of inhalation, exhalation, and breath holding. For example, it normally takes a human being about three to four seconds to complete one respiratory period. Certainly, the respiratory period may change in a special case or pathological state. In the present embodiment, the patient may be provided with respiratory training to acquire an initial respiratory period of the patient as a preset respiratory period of the patient. Certainly, the respiratory period of the patient may be acquired in another manner.

Figure 7:
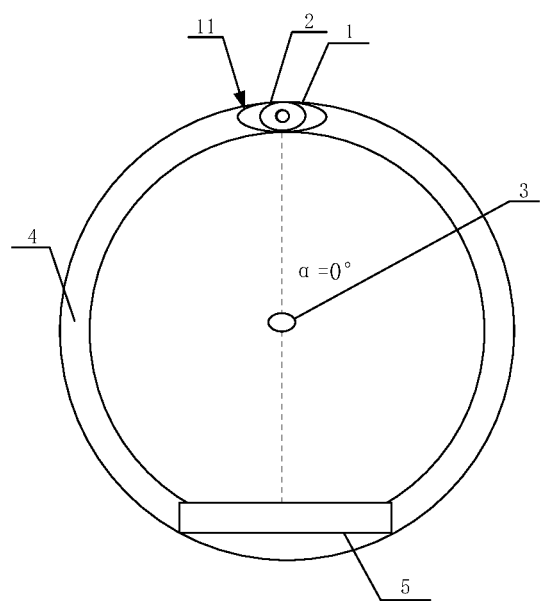
FIG. 7 is a schematic diagram showing that an angle between a first ray source and a second ray source is 0° according to an embodiment of the present disclosure.

In an example of the present embodiment, as shown in FIG. 7, the angle α between the first ray source 1 and the second ray source 2 may further be 0°. In this case, the direction of the ray received by the detector and the direction of the ray of the second ray source are in one straight line. The photographed image is a corresponding image during the ray irradiation of the second ray source. In this case, a location change of a tumor no matter caused by a respiratory movement or caused by the movement of the patient's body can both be detected by the detector in real time with high precision.

Figure 8:
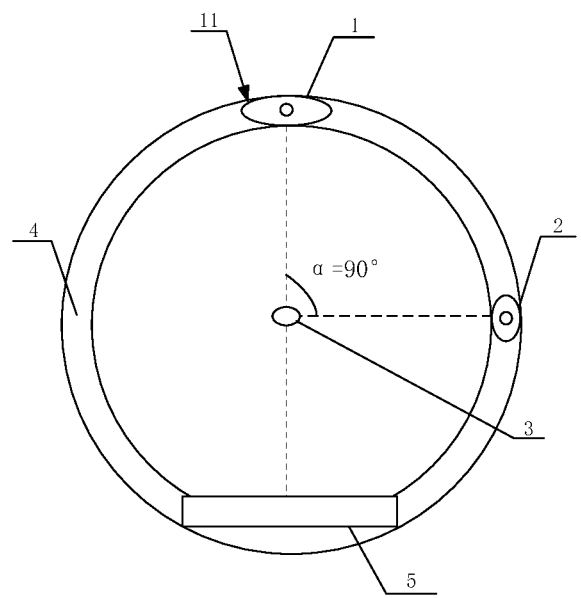
FIG. 8 is a schematic diagram showing that an angle between a first ray source and a second ray source is 90° according to an embodiment of the present disclosure.

In an example of the present embodiment, as shown in FIG. 8, the angle α between the first ray source 1 and the second ray source 2 may be 90°. That is, the first ray source 1 and the second ray source 2 are orthogonal to each other. In this case, the direction of the ray received by the detector and the direction of the ray of the second ray source are perpendicular to each other. The photographed image has an orthogonal relationship with a planar image during ray irradiation by a treatment source. In this case, image data acquired from two perpendicular angles can be used to obtain three-dimensional location information of a tumor, and then precise three-dimensional location information of the tumor can be determined.

Figure 9:
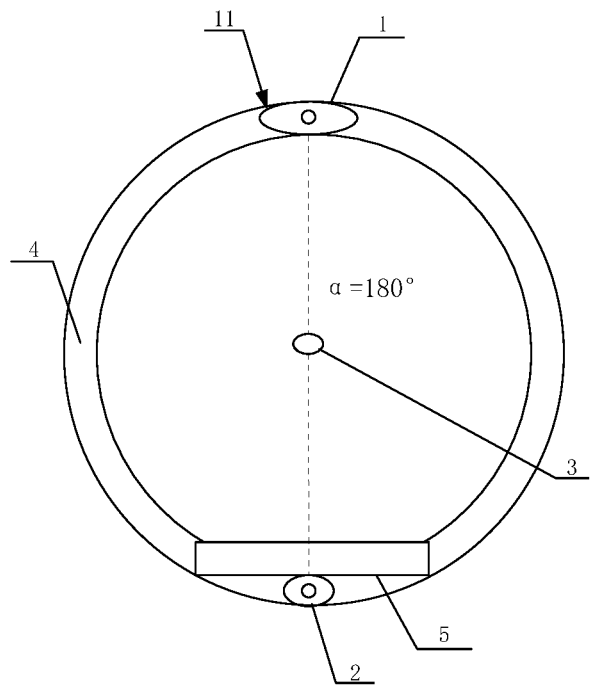
FIG. 9 is a schematic diagram showing that an angle between a first ray source and a second ray source is 180° according to an embodiment of the present disclosure.

In an example of the present embodiment, as shown in FIG. 9, the angle α between the first ray source 1 and the second ray source 2 may be 180°. In this case, the direction of the ray received by the detector is opposite to the direction of the ray of the second ray source and they are mirror images of each other. In this case, location information of a tumor in the first image data determined according to the first ray source is a location in a two-dimensional plane, and a mapping between the second ray source and the first ray source is used to perform precise irradiation on a planar location of the tumor.

In the present embodiment, the angle α between the first ray source 1 and the second ray source 2 may be other angle, for example, 10°, 25°, 30°, 31°, 35°, 45°, 50°, 60°, 66°, 79°, 88°, 92°, 100°, 120°, 140°, 155°, 176° and so on, and may be set according to an actual requirement. When the angle α between the first ray source 1 and the second ray source 2 is closer to 0° or 180°, an image formed by a diagnosis source is closer to an actual image during the treatment of the treatment source, such that the treatment precision can be further improved.

In an example of the present embodiment, the first ray source and the second ray source may rotate around the patient in a circumferential direction. The first ray source and the second ray source may have the same rotational velocity or may have different rotational velocities. For example, both the first ray source and the second ray source are disposed on a drum and driven by the drum to rotate, and thus have the same rotational velocity. Alternatively, the first ray source and the second ray source are separately supported by cantilevers and driven by the cantilevers to rotate, and thus have different rotational velocities.

In an example of the present embodiment, the first ray source and the second ray source may be mounted on a drum, and the method of the present embodiment further includes: setting a rotational velocity of the first ray source, wherein the rotational velocity is: $x=(\alpha/NT)$, x is a rotational angular velocity, a is an angle between the first ray source and the second ray source, T is the respiratory period of the patient, and N is a multiple between the time taken for the second ray source to move to the first location and the preset respiratory period. Certainly, a rotational velocity of the second ray source may further be set, wherein the rotational velocity of the second ray source is: $x'=(\alpha/NT)$, x' is a rotational angular velocity of the second ray source, a is an angle between the first ray source and the second ray source, T is the respiratory period of the patient, and N is a multiple between the time taken for the second ray source to move to the first location and the preset respiratory period.

In step S103 of the present embodiment, the adjusting the second ray source according to the first image data includes: adjusting an irradiation angle, a dosage or a dose distribution of the second ray source according to the first image data. In this way, data such as the irradiation angle, dosage, and dose distribution of the second ray source is adjusted based on the first image data at the same nodes within the different respiratory periods, and thus the target can be irradiated by the second ray source more precisely and the irradiation to the normal tissue around a diseased part can be reduced.

Figure 10:
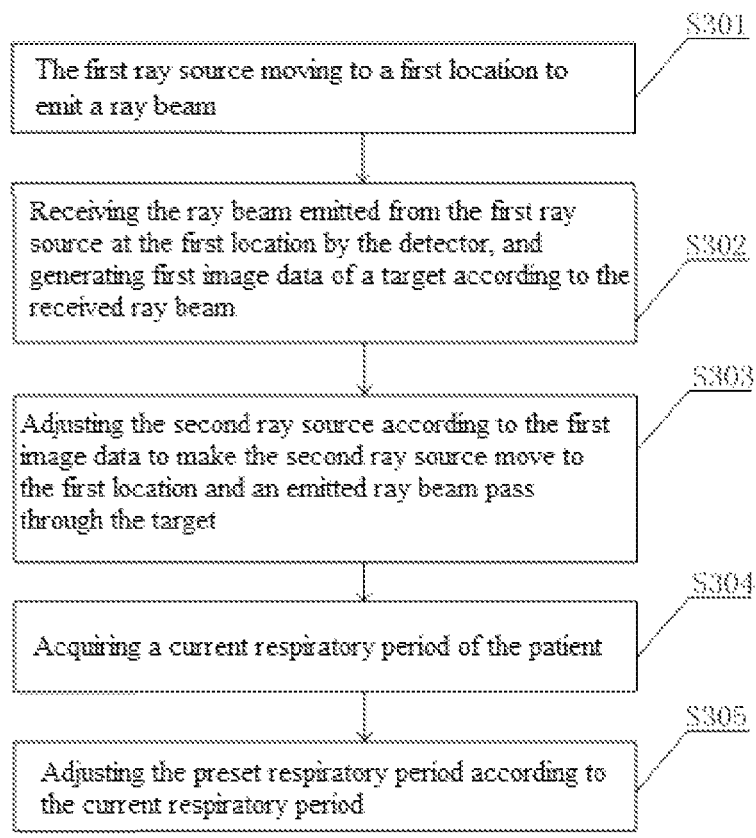
FIG. 10 is a flowchart of still another target tracking and irradiation method using a radiotherapy apparatus according to an embodiment of the present disclosure.

In an example of the present embodiment, as shown in FIG. 10, the method of the present embodiment includes the following steps S301-S305:

In S301, the first ray source moves to a first location to emit a ray beam.

In S302, the detector receives the ray beam emitted from the first ray source at the first location, and generates first image data of a target according to the received ray beam.

In S303, the second ray source is adjusted according to the first image data to make the second ray source move to the first location and an emitted ray beam pass through the target, wherein a time taken for the second ray source to move to the first location is a positive integer multiple of a preset respiratory period of a patient.

In S304, a current respiratory period of the patient is acquired.

In S305, the preset respiratory period is adjusted according to the current respiratory period.

Before the patient is treated, the respiratory period of the patient may be acquired in a manner such as respiratory training, to obtain the preset respiratory period. In the beginning of the treatment of the patient, the preset respiratory period may be used to perform radioactive treatment, imaging or the like on the patient. For more precise treatment, the current respiratory period of the patient may be acquired. In this way, it may be known whether the respiratory period of the patient changes. If a change occurs, the acquired current respiratory period of the patient is used to replace the preset respiratory period in step S303, such that the respiratory period is more accurate and more precise data is provided for treatment. For example, the respiratory period of the patient acquired before treatment is 4 seconds. The acquired current respiratory period of the patient is 4.2 seconds. In this case, the previous preset respiratory period of 4 seconds is changed to the current respiratory period of 4.2 seconds to facilitate more precise treatment. In the present embodiment, for a manner of acquiring the current respiratory period of the patient, the patient in the current status is provided with respiratory training to acquire the current respiratory period of the patient. Alternatively, acquired image data is analyzed to acquire the current respiratory period. Certainly, the current respiratory period may be acquired in another manner. A specific manner of acquiring the respiratory period of the patient is not limited in the present embodiment. For example, a respiratory monitoring device is used to acquire the respiratory period. The preset respiratory period is a respiratory period initially input and set in a system and may be an average respiratory period of patients. The preset respiratory period may be a respiratory period of the patient obtained after a physician trains the patient. The preset respiratory period is a trained respiratory period of a patient as an example for description in the present disclosure.

Certainly, step 304 and step 305 are not limited to the foregoing specific example. For example, the current respiratory period may be acquired before the first ray source moves, and the current respiratory period is adjusted to be the preset respiratory period.

Figure 11:
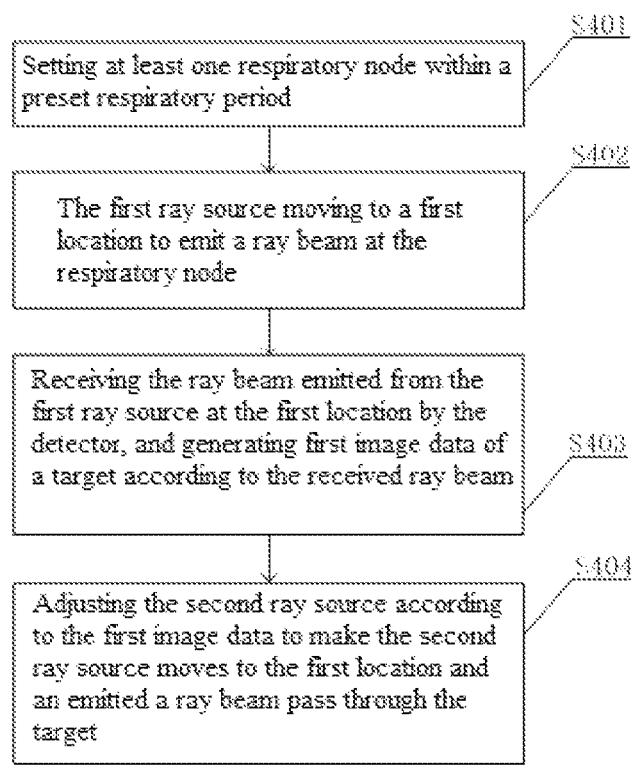
FIG. 11 is a flowchart of yet another target tracking and irradiation method using a radiotherapy apparatus according to an embodiment of the present disclosure.

In the present embodiment, what is shown in FIG. 1 is used as an example. For example, as shown in FIG. 11, the method includes the following steps S401-S404.

In S401, at least one respiratory node within a preset respiratory period is set.

In S402, the first ray source moves to a first location to emit a ray beam at the respiratory node.

In S403, the detector receives the ray beam emitted from the first ray source at the first location, and generates first image data of a target according to the received ray beam.

In S404, the second ray source is adjusted according to the first image data to make the second ray source moves to the first location and an emitted a ray beam pass through the target, wherein a time taken for the second ray source to move to the first location is a positive integer multiple of a preset respiratory period of a patient.

In this manner, the first ray source may be controlled to emit a ray beam at a preset respiratory node, and the detector receives the ray beam to acquire image data. Next, the image data may be compared with image data at other same respiratory nodes or different respiratory nodes. In this manner, the current status of the patient may be compared with a previous status at the same nodes, it may be determined whether the respiratory period of the patient changes or not, and a specific value of a change in the respiratory period may be specifically determined by using the extent of a location change, thereby acquiring the current respiratory period of the patient. After the current respiratory period of the patient is acquired, the acquired current respiratory period of the patient may be used to replace the previous preset respiratory period so that the respiratory period is more accurate and more precise data is provided for treatment. Therefore, the current respiratory period of the patient may be acquired in this manner in the present embodiment, so as to provide more precise data for treatment. In the present embodiment, the respiratory node may be any node, for example, T/5, T/4, T/2, 5T/8, 3T/4 or 5T/6. The method used in the present embodiment can rapidly obtain a current respiratory period of the patient, which is convenient for implementation and use in treatment.

In an embodiment provided by the present disclosure, the method further includes the following steps.

Within one respiratory period, the first ray source emits ray beams at a plurality of different first locations at respective respiratory nodes.

The detector respectively receives the ray beams emitted from the first ray source at the first locations, and respectively generates a plurality of first image data of the target according to the received ray beams.

Movement trajectory information of the target is acquired within the respiratory period according to the plurality of first image data.

For example, the first ray source respectively emits ray beams at a plurality of locations corresponding to a plurality of nodes of T/2, T/4, and T/8 within one respiratory period. The detector respectively receives the ray beams from the first ray source at the nodes to generate a plurality of first image data. In this way, a movement trajectory of the target within the respiratory period can be obtained according to the data at the plurality of nodes. In addition, the more respiratory nodes are set, the more precise the movement trajectory is obtained.

In addition, after the movement trajectory information of the target within the respiratory period is acquired, a current respiratory period of a patient may be calculated according to the movement trajectory information, so as to use the current respiratory period of the patient to replace a preset respiratory period to implement more accurate imaging, treatment or the like on the patient.

In an example of the present embodiment, the method further includes: acquiring first image data at same respiratory nodes within different respiratory periods; the adjusting the second ray source according to the first image data includes: adjusting the second ray source according to the first image data at the same respiratory nodes within the different respiratory periods.

Figure 12:
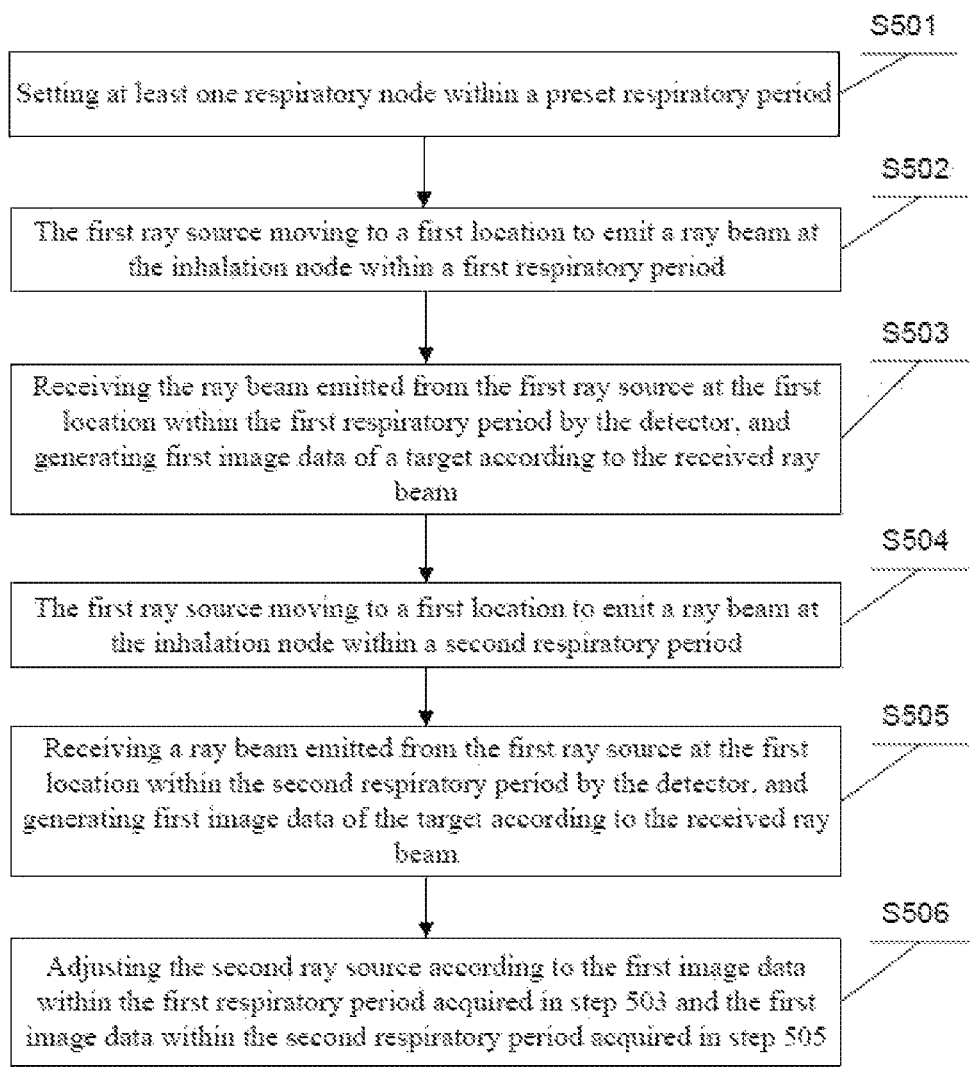
FIG. 12 is a flowchart of a further target tracking and irradiation method using a radiotherapy apparatus according to an embodiment of the present disclosure.

For example, FIG. 10 is used as an example. Referring to FIG. 12, in an embodiment provided by the present disclosure, the method includes the following steps S501-S506.

In S501, at least one respiratory node, for example, an inhalation node, within a preset respiratory period is set.

In S502, within a first respiratory period, the first ray source moves to a first location to emit a ray beam at the inhalation node.

In S503, the detector receives the ray beam emitted from the first ray source at the first location within the first respiratory period, and generates first image data of a target according to the received ray beam.

In S504, within a second respiratory period, the first ray source moves to the first location to emit a ray beam at the inhalation node.

In S505, the detector receives a ray beam emitted from the first ray source at a first location within a second respiratory period, and generates first image data of the target according to the received ray beam.

In S506, the second ray source is adjusted according to the first image data within the first respiratory period acquired in step 503 and the first image data within the second respiratory period acquired in step 505.

In this manner, a change in a target and a status of the target can be obtained more accurately from the first image data of the same respiratory nodes within different respiratory periods, so as to precisely adjust the second ray source, such as an irradiation angle, a dosage, a dose distribution, and the like, to make the second ray source more closely match an actual status of the target and reduce the irradiation of the normal tissue around a diseased part. In addition, the method of the present embodiment can also compare the first image data at the same respiratory nodes within the different respiratory periods, thereby determining whether the respiratory period of the patient changes, and obtaining the extent of the change by image data and a current respiratory period of the patient. The different respiratory periods may be two adjacent respiratory periods or three or more than three adjacent respiratory periods or any two or three or more than three nonadjacent respiratory periods. For example, the different respiratory periods are two adjacent respiratory periods. In this case, it may be determined whether the respiratory period of the patient changes within a short time and the detail of the change can be found out. For another example, the different respiratory periods are three or more than three adjacent respiratory periods. In this case, a change in the respiratory period and the value of the current respiratory period of the patient are more accurately obtained by comparing more image data. For another example, the different respiratory periods are any two nonadjacent respiratory periods. In this case, respiratory changes of the patient within the different periods of time are obtained by comparing the respiratory periods of the patient within different periods of time, so as to provide more rich data for treatment. For another example, the different respiratory periods are any three or more than three nonadjacent respiratory periods. In this case, more changes in the respiratory periods of the patient within different periods of time can be obtained, so as to learn more precisely about changes in the pathological status of the patient.

In an example of the present embodiment, the method further includes: acquiring first image data within at least two different respiratory periods; determining location information of the target according to the first image data within the different respiratory periods; and the adjusting the second ray source according to the first image data includes: adjusting the second ray source according to the location information of the target.

Figure 13:
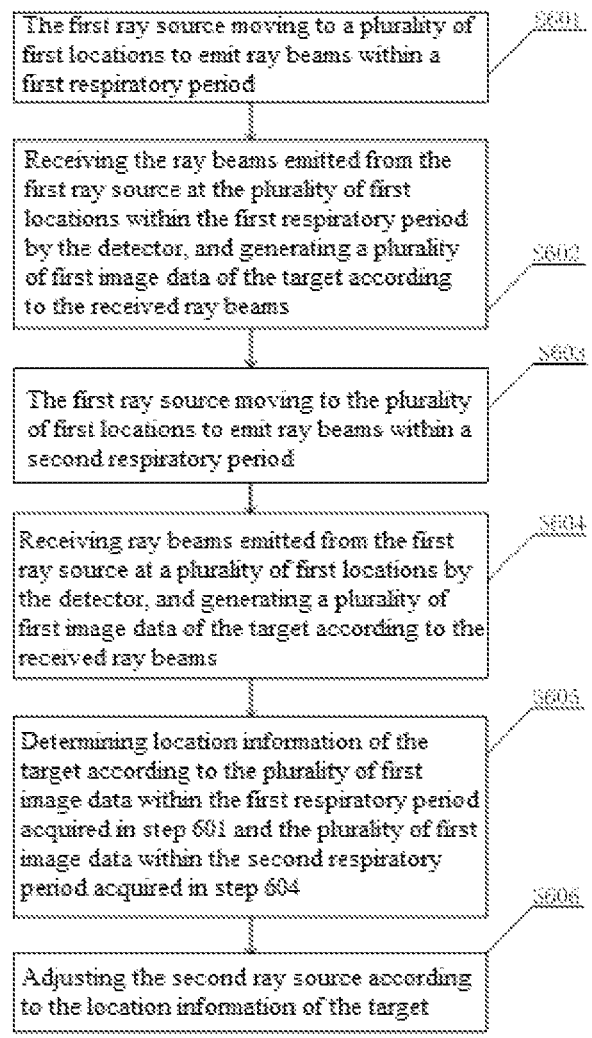
FIG. 13 is a flowchart of still a further target tracking and irradiation method using a radiotherapy apparatus according to an embodiment of the present disclosure.

For example, referring to FIG. 13, an embodiment provided by the present disclosure includes the following steps S601-S606.

In S601, within a first respiratory period, the first ray source moves to a plurality of first locations to emit ray beams.

In S602, the detector receives the ray beams emitted from the first ray source at the plurality of first locations within the first respiratory period, and generates a plurality of first image data of the target according to the received ray beams.

In S603, within a second respiratory period, the first ray source moves to the plurality of first locations to emit ray beams.

In S604, the detector receives ray beams emitted from the first ray source at a plurality of first locations, and generates a plurality of first image data of the target according to the received ray beams.

In S605, location information of the target is determined according to the plurality of first image data within the first respiratory period acquired in step 601 and the plurality of first image data within the second respiratory period acquired in step 604.

In S606, the second ray source is adjusted according to the location information of the target.

In this manner, location information of a target may be precisely acquired, and the second ray source can be adjusted according to the location information, so that the second ray source can irradiate the location of the target more accurately and reduce damage to normal tissue. In this manner, the change of the target may further be obtained by the first image data within at least two different respiratory periods, so as to obtain a current respiratory period of a patient, and then the acquired current respiratory period of the patient may then be used to replace a previous preset respiratory period, thereby making the respiratory period more accurate and providing more precise data for treatment.

The present disclosure provides an apparatus corresponding to the foregoing method. The apparatus may perform the functions in the foregoing method. Therefore, some descriptions in the foregoing method are not repeated below again.

Figure 14:
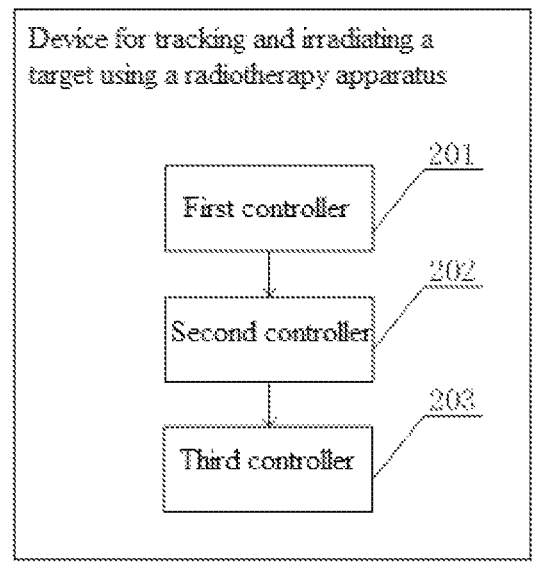
FIG. 14 is a schematic diagram of a target tracking and irradiation device using a radiotherapy apparatus according to an embodiment of the present disclosure.

As shown in FIG. 14, an embodiment of the present disclosure discloses a target tracking and irradiation device using a radiotherapy apparatus. Referring to FIG. 2, the radiotherapy apparatus includes a first ray source 1, a second ray source 2, and at least one detector 5. The device includes a first controller 201, a second controller 202, and a third controller 203.

The first controller 201 is configured to control the movement of the first ray source, wherein the first ray source moves to a first location to emit a ray beam.

The second controller 202 is configured to control the detector to receive the ray beam emitted from the first ray source at the first location, and generate first image data of a target according to the received ray beam.

The third controller 203 is configured to receive the first image data of the detector and adjust the second ray source according to the first image data to make the second ray source move to the first location and an emitted ray beam pass through the target.

The third controller is further configured to control a time taken for the second ray source to move to the first location to be a positive integer multiple of a preset respiratory period of a patient.

In this manner, the first ray source emits a ray beam at the first location, the detector receives the ray beam to form first image data of a target, the second ray source is then adjusted according to the first image data, and the second ray source is controlled to move to the first location to emit a ray beam. Because the time taken for the second ray source to move to the first location is a positive integer multiple of a preset respiratory period of a patient, a node during an irradiation of the first ray source emits radiation and a node during an irradiation of the second ray source emits radiation are the same nodes within different respiratory periods. Therefore, a state that the target is in when the second ray source irradiates the target at the first location and a state that the target is in when the target receives radiation from the first ray source are highly similar. Therefore, controlling the second ray source to irradiate the target with reference to the first image data greatly reduces the errors caused by the patient's respiration, and more accurately irradiates the target location, so that a ray beam can always irradiate the location of a tumor and normal tissue is avoided from being irradiating and thus damage to the normal tissue is reduced.

For example, the first location may include at least two different locations. The present embodiment discloses a target tracking and irradiation device using a radiotherapy apparatus. What is shown in FIG. 14 is used as an example. The device includes a first controller 201, a second controller 202, and a third controller 203.

The first controller 201 is configured to control the movement of the first ray source, wherein within a first respiratory period, the first ray source is controlled to move to the first location to emit a ray beam; and within a second respiratory period, the first ray source is controlled to move to a first location to emit a ray beam.

The second controller 202 is configured to control the detector to receive the ray beam emitted from the first ray source at the first location within the first respiratory period and generate first image data of a target according to the received ray beam; and receive the ray beam emitted from the first ray source at the first location within the second respiratory period and generate first image data of the target according to the received ray beam.

The third controller 203 is configured to adjust the second ray source according to the first image data within the first respiratory period to make the second ray source move to the first location and an emitted ray beam pass through the target; and adjust the second ray source according to the first image data within the second respiratory period to make the second ray source move to the first location and an emitted ray beam pass through the target.

The third controller is further configured to control a time taken for the second ray source to move to the first location to be a positive integer multiple of a preset respiratory period of a patient.

The device further includes a fourth processor configured to determine location information of the target according to the first image data within the first respiratory period and the second respiratory period.

In an embodiment provided by the present disclosure, first image data within at least two different respiratory periods is acquired, location information of the target is determined according to the first image data within the different respiratory periods, and the second ray source is adjusted according to the location information of the target. The first image data within two different respiratory periods is used to precisely acquire the location information of the target, and thus to adjust the second ray source according to the location information, make the second ray source to irradiate the location of the target more accurately and reduce damage to normal tissue.

In an example of the present embodiment, the first ray source and the second ray source may be mounted on a drum, and the first controller in the present embodiment is further configured to control a rotational velocity of the first ray source, wherein the rotational velocity is: x=(α/NT), x is a rotational angular velocity, a is an angle between the first ray source and the second ray source, T is the respiratory period of the patient, and N is a multiple between the time taken for the second ray source to move to the first location and the preset respiratory period. Certainly, the third controller may control a rotational velocity of the second ray source, wherein the rotational velocity of the second ray source is: x'=(α/NT), wherein x' is a rotational angular velocity of the second ray source, a is an angle between the first ray source and the second ray source, T is the respiratory period of the patient, and N is a multiple between the time taken for the second ray source to move to the first location and the preset respiratory period.

In the present embodiment, the third controller adjusting the second ray source according to the first image data includes: adjusting an irradiation angle, a dosage or a dose distribution of the second ray source according to the first image data. In this way, data such as the irradiation angle, dosage and dose distribution of the second ray source is adjusted based on the first image data at the same nodes within the different respiratory periods, and thus the target can be irradiated by the second ray source more precisely and the irradiation to the normal tissue around a diseased part can be reduced.

In an example of the present embodiment, please refer to FIG. 14, the device in the present embodiment includes a first controller 201, a second controller 202, a third controller 203 and a sixth processor.

The first controller 201 is configured to control the movement of the first ray source, wherein the first ray source moves to a first location to emit a ray beam.

The second controller 202 is configured to control the detector to receive the ray beam emitted from the first ray source at the first location, and generate first image data of a target according to the received ray beam.

The third controller 203 is configured to receive the first image data of the detector and adjust the second ray source according to the first image data to make the second ray source move to the first location and an emitted ray beam pass through the target, wherein a time taken for the second ray source to move to the first location is a positive integer multiple of a preset respiratory period of a patient.

The sixth processor is configured to acquire a current respiratory period of the patient and adjust the preset respiratory period according to the current respiratory period.

Before the patient is treated, the respiratory period of the patient may be acquired in a manner such as respiratory training, to obtain the preset respiratory period. In the beginning of the treatment of the patient, the preset respiratory period may be used to perform radioactive treatment, imaging or the like on the patient. For more precise treatment, the current respiratory period of the patient may be acquired. In this way, it may be known whether the respiratory period of the patient changes. If a change occurs, the acquired current respiratory period of the patient is used to replace the preset respiratory period, such that the respiratory period is more accurate and more precise data is provided for treatment.

Figure 15:
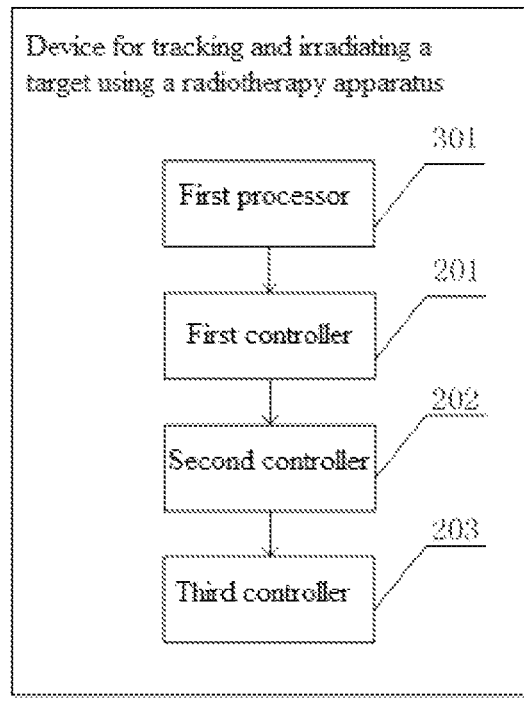
FIG. 15 is a schematic diagram of another target tracking and irradiation device using a radiotherapy apparatus according to an embodiment of the present disclosure.

In the present embodiment, what is shown in FIG. 14 is used as an example. As shown in FIG. 15, for example, the device includes a first processor 301, a first controller 201, a second controller 202 and a third controller 203.

The first processor 301 is configured to set at least one respiratory node within a preset respiratory period.

The first controller 201 is configured to control the movement of the first ray source, wherein the first ray source moves to a first location to emit a ray beam at the at least one respiratory node within the preset respiratory period.

The second controller 202 is configured to control the detector to receive the ray beam emitted from the first ray source at the first location, and generate first image data of a target according to the received ray beam.

The third controller 203 is configured to receive the first image data of the detector, and adjust the second ray source according to the first image data to make the second ray source move to the first location and an emitted ray beam pass through the target, wherein a time taken for the second ray source to move to the first location is a positive integer multiple of a preset respiratory period of a patient.

In this manner, the first ray source may be controlled to emit a ray beam at a preset respiratory node, and the detector receives the ray beam to acquire image data. Next, the image data may be compared with image data at other same respiratory nodes or different respiratory nodes. In this manner, the current status of the patient may be compared with a previous status at the same nodes, it may be determined whether the respiratory period of the patient changes or not, and a specific value of a change in the respiratory period may be specifically determined by using the extent of a location change, thereby acquiring the current respiratory period of the patient.

In an embodiment provided by the present disclosure, for example, the first controller is further configured to, within one respiratory period, control the first ray source to emit ray beams at a plurality of different first locations at respective respiratory nodes.

The second controller is further configured to control the detector to respectively receive the ray beams emitted from the first ray source at the first locations, and respectively generate a plurality of first image data of the target according to the received ray beams.

The device further includes a second processor, configured to acquire movement trajectory information of the target within the respiratory period according to the plurality of first image data.

For example, the first ray source respectively emits ray beams at a plurality of locations corresponding to a plurality of nodes of T/2, T/4, and T/8 within one respiratory period. The detector respectively receives the ray beams from the first ray source at the nodes to generate a plurality of first image data. In this way, a movement trajectory of the target within the respiratory period can be obtained according to the data at the plurality of nodes. In addition, after the movement trajectory information of the target within the respiratory period is acquired, a current respiratory period of a patient may be calculated according to the movement trajectory information, so as to use the current respiratory period of the patient to replace a preset respiratory period to implement more accurate imaging, treatment or the like on the patient.

In an example of the present embodiment, the device further includes a third processor, configured to acquire first image data at same respiratory nodes within different respiratory periods.

The third controller is specifically configured to adjust the second ray source according to the first image data at the same respiratory nodes within the different respiratory periods.

For example, what is shown in FIG. 14 is used as an example. In an embodiment provided by the present disclosure, the device includes a first controller 201, a second controller 202, and a third controller 203.

The first controller 201 is configured to control the movement of the first ray source, wherein within a first respiratory period, the first ray source moves to a first location to emit a ray beam at at least one respiratory node, for example, an inhalation node, within a preset respiratory period; and within a second respiratory period, the first ray source moves to the first location to emit a ray beam at the inhalation node.

The second controller 202 is configured to control the detector to receive the ray beam emitted from the first ray source at the first location within the first respiratory period and generate first image data of a target according to the received ray beam; and control the detector to receive a ray beam emitted from the first ray source at a first location within the second respiratory period and generate first image data of the target according to the received ray beam.

The third controller 203 is configured to adjust the second ray source according to the acquired first image data within the first respiratory period and first image data within the second respiratory period.

In this manner, a change in a target and a status of the target can be obtained more accurately from the first image data of the same respiratory nodes within different respiratory periods, so as to precisely adjust the second ray source, such as an irradiation angle, a dosage, a dose distribution, and the like, to make the second ray source more closely match an actual status of the target, and reduce the irradiation of the normal tissue around a diseased part. In addition, the method of the present embodiment can also compare the first image data at the same respiratory nodes within the different respiratory periods, thereby determining whether the respiratory period of the patient changes, and obtaining the extent of the change by image data and a current respiratory period of the patient.

In an example of the present embodiment, the fourth processor is configured to acquire first image data within at least two different respiratory periods; and determine location information of the target according to the first image data within the different respiratory periods.

The third controller is specifically configured to adjust the second ray source according to the location information of the target.

For example, referring to FIG. 14, an embodiment provided by the present disclosure includes a first controller 201, a second controller 202, and a third controller 203.

The first controller 201 is configured to control the movement of the first ray source, wherein within a first respiratory period, the first ray source moves to a plurality of first locations to emit ray beams; and within a second respiratory period, the first ray source moves to the plurality of first locations to emit ray beams.

The second controller 202 is configured to control the detector to receive the ray beams emitted from the first ray source at the plurality of first locations within the first respiratory period, and generate a plurality of first image data of the target according to the received ray beams; and control the detector to receive ray beams emitted from the first ray source at a plurality of first locations, and generate a plurality of first image data of the target according to the received ray beams.

The third controller 203 is configured to determine location information of the target according to the acquired plurality of first image data within the first respiratory period and the plurality of first image data within the second respiratory period; and adjust the second ray source according to the location information of the target.

In this manner location information of a target may be precisely acquired, and the second ray source can be adjusted according to the location information, so that the second ray source can irradiate the location of the target more accurately and reduce damage to normal tissue. In this manner, the change of the target may further be obtained by the first image data within at least two different respiratory periods, so as to obtain a current respiratory period of a patient, and then the acquired current respiratory period of the patient may then be used to replace a previous preset respiratory period, thereby making the respiratory period more accurate and providing more precise data for treatment.

A radiotherapy apparatus is provided in an embodiment of the present disclosure. The radiotherapy apparatus includes any one of the foregoing target tracking and irradiation devices using a radiotherapy apparatus.

The foregoing content is more detailed descriptions of the present disclosure with reference to specific preferred implementations. It should not be considered that specific implementations of the present disclosure are only limited to these descriptions. A person of ordinary skill in the art of the present disclosure may further make simple deductions or replacements without departing from the concept of the present disclosure, and these deductions or replacements shall all be construed as falling within the protection scope of the present disclosure.

What is claimed is:

1. A target tracking and irradiation method using a radiotherapy apparatus, the radiotherapy apparatus comprising a first ray source, a second ray source and at least one detector, wherein the method comprises:
moving the first ray source to a first location to emit a ray beam;
receiving the ray beam emitted from the first ray source at the first location and generating first image data of a target according to the received ray beam, by the detector; and
adjusting the second ray source according to the first image data to make the second ray source move to the first location and an emitted ray beam pass through the target, wherein a time taken for the second ray source to move to the first location is a positive integer multiple of a preset respiratory period of a patient,
wherein the method further comprises: setting at least one respiratory node within the preset respiratory period,
wherein the moving the first ray source to the first location to emit the ray beam comprises:
moving the first ray source to the first location to emit the ray beam at the respiratory node, and
wherein the method further comprises:
respectively emitting, by the first ray source, the ray beam at a plurality of different first locations and at each respiratory node within one respiratory period;
respectively receiving the ray beam emitted by the first ray source at each first location and respectively generating a plurality of first image data of the target according to the received ray beam, by the detector; and
acquiring movement trajectory information of the target within the respiratory period according to the plurality of first image data.

2. The method according to claim 1, wherein the method further comprises:
acquiring first image data at same respiratory nodes within different respiratory periods; and
the adjusting the second ray source according to the first image data comprises: adjusting the second ray source according to the first image data at the same respiratory nodes within the different respiratory periods.

3. The method according to claim 1, wherein the method further comprises:
acquiring first image data within at least two different respiratory periods;
determining location information of the target according to the first image data within the different respiratory periods; and
the adjusting the second ray source according to the first image data comprises: adjusting the second ray source according to the location information of the target.

4. The method according to claim 1, wherein the method further comprises:
receiving the ray beam emitted by the second ray source at the first location and generating second image data of the target according to the received ray beam, by the detector; and
confirming the first image data and the second image data.

5. The method according to claim 1, wherein the method further comprises:
acquiring a current respiratory period of the patient; and
adjusting the preset respiratory period according to the current respiratory period.

6. The method according to claim 1, wherein the first ray source and the second ray source rotating around the patient in a circumferential direction; the method further comprises: setting a rotational velocity of the first ray source, wherein the rotational velocity is: $x=(\alpha/NT)$
wherein x is a rotational angular velocity, $\alpha$ is an angle between the first ray source and the second ray source, T is the respiratory period of the patient, and N is a multiple between the time taken for the second ray source to move to the first location and the preset respiratory period.

7. The method according to claim 1, wherein the adjusting the second ray source according to the first image data comprises:
adjusting an irradiation angle, a dosage or a dose distribution of the second ray source according to the first image data.

8. The method according to claim 1, wherein an angle between the first ray source and the second ray source is 0° or 180°.

9. A target tracking and irradiation device for use in a radiotherapy apparatus, the radiotherapy apparatus comprising a first ray source, a second ray source, and at least one detector; wherein the device comprises:
a first controller configured to control the movement of the first ray source, wherein the first ray source moves to a first location to emit a ray beam;
a second controller configured to control the detector to receive the ray beam emitted by the first ray source at the first location, and generate first image data of a target according to the received ray beam; and
a third controller configured to receive the first image data of the detector and adjust the second ray source according to the first image data to make the second ray source move to the first location and an emitted ray beam pass through the target; and
wherein the third controller is further configured to control a time taken for the second ray source to move to the first location to be a positive integer multiple of a preset respiratory period of a patient,
wherein the device further comprises a first processor configured to acquire at least one set respiratory node within the preset respiratory period,
wherein the first controller is specifically configured to control the first ray source to move to the first location to emit the ray beam at the respiratory node,
wherein the first controller is further configured to control the first ray source to respectively emit the ray beam at a plurality of different first locations and at each respiratory node within one respiratory period,
wherein the second controller is further configured to control the detector to respectively receive the ray beam emitted by the first ray source at the first locations, and respectively generate a plurality of first image data of the target according to the received ray beam, and
wherein the device further comprises a second processor configured to acquire movement trajectory information of the target within the respiratory period according to the plurality of first image data.

10. The device according to claim 8, wherein the device further comprises:
a third processor, configured to acquire first image data at same respiratory nodes within different respiratory periods; and wherein the third controller is specifically configured to adjust the second ray source according to the first image data at the same respiratory nodes within the different respiratory periods acquired by the third processor.

11. The device according to claim 8, wherein the device further comprises a fourth processor, configured to acquire first image data within at least two different respiratory periods and determine location information of the target according to the first image data within the different respiratory periods; and wherein the third controller is specifically configured to adjust the second ray source according to the location information of the target determined by the fourth processor.

12. The device according to claim 8, wherein the second controller is further configured to control the detector to receive the ray beam emitted by the second ray source at the first location, and generate second image data of the target according to the received ray beam; and wherein the device further comprises a fifth processor configured to confirm the first image data and the second image data.

13. The device according to claim 9, wherein the device further comprises a sixth processor configured to acquire a current respiratory period of the patient and adjust the preset respiratory period according to the current respiratory period.

14. The device according to claim 9, wherein the first ray source and the second ray source rotate around the patient in a circumferential direction; the first controller is further configured to control a rotational velocity of the first ray source, wherein the rotational velocity is:

x=($\alpha$/NT), wherein x is a rotational angular velocity, $\alpha$ is an angle between the first ray source and the second ray source, T is the respiratory period of the patient, and N is a multiple between the time taken for the second ray source to move to the first location and the preset respiratory period.

15. The device according to claim 9, wherein the third controller is specifically configured to adjust an irradiation angle, a dosage or a dose distribution of the second ray source according to the first image data.

16. A radiotherapy apparatus, wherein the radiotherapy apparatus comprises the device according to claim 9.

* * * * *

UNITED STATES PATENT AND TRADEMARK OFFICE
CERTIFICATE OF CORRECTION

PATENT NO. : 11,241,589 B2
APPLICATION NO. : 16/624881
DATED : February 8, 2022
INVENTOR(S) : Li et al.

It is certified that error appears in the above-identified patent and that said Letters Patent is hereby corrected as shown below:

In the Specification

In Column 10, Line 21, delete "a" and insert -- α --.

In Column 10, Line 28, delete "a" and insert -- α --.

In Column 15, Line 48, delete "a" and insert -- α --.

In Column 15, Line 56, delete "a" and insert -- α --.

In the Claims

In Column 20, Claim 10, Line 63, delete "claim 8," and insert -- claim 9, --.

In Column 21, Claim 11, Line 6, delete "claim 8," and insert -- claim 9, --.

In Column 21, Claim 12, Line 16 (Approx.), delete "claim 8," and insert -- claim 9, --.

Signed and Sealed this
Nineteenth Day of July, 2022

Katherine Kelly Vidal
*Director of the United States Patent and Trademark Office*